United States Patent
Wohlwend

[19]

[11] Patent Number: 6,106,747
[45] Date of Patent: Aug. 22, 2000

[54] PROCESS FOR MANUFACTURING PROSTETIC DENTAL RECONSTRUCTIONS

[76] Inventor: Arnold Wohlwend, Gartenstrasse 5, CH-8903 Birnensdorf, Switzerland

[21] Appl. No.: 08/930,028

[22] PCT Filed: Mar. 28, 1996

[86] PCT No.: PCT/EP96/01367

§ 371 Date: Nov. 21, 1997

§ 102(e) Date: Nov. 21, 1997

[87] PCT Pub. No.: WO96/29951

PCT Pub. Date: Oct. 3, 1996

[30] Foreign Application Priority Data

Mar. 28, 1995 [DE] Germany ............... 195 11 396

[51] Int. Cl.[7] .................... A61C 13/00; A61C 13/08; C04B 33/32
[52] U.S. Cl. ................ 264/16; 264/17; 264/19; 264/672; 264/673
[58] Field of Search ................ 264/16, 17, 19, 264/672, 673

[56] References Cited

U.S. PATENT DOCUMENTS

| | | | |
|---|---|---|---|
| 4,634,561 | 1/1987 | DeLuca | 264/17 |
| 5,106,303 | 4/1992 | Oden et al. | 433/223 |
| 5,192,472 | 3/1993 | Anderson | 264/40.1 |
| 5,565,152 | 10/1996 | Oden et al. | 264/19 |

FOREIGN PATENT DOCUMENTS

| | | |
|---|---|---|
| 0389461 | 9/1990 | European Pat. Off. . |
| 0477157 | 3/1992 | European Pat. Off. . |
| 0580565 | 1/1994 | European Pat. Off. . |

*Primary Examiner*—Christopher A. Fiorilla
*Attorney, Agent, or Firm*—Rothwell, Figg, Ernst & Kurz, p.c.

[57] ABSTRACT

A method for producing a dental prosthesis to be fitted to a fitting member including the steps of: determining the three-dimensional contours of the fitting member; producing a three-dimensional form of the dental prosthesis; producing a working stump and/or a working pack; placing the working stump in the form and/or packing the working pack around the outside of the form to completely cover the form; sintering the form with the working stump and/or the working pack; and separating the working stump and/or the working pack from the dental prosthesis after sintering. The working stump and working pack are produced such that they are enlarged by a predetermined enlargement factor.

8 Claims, 2 Drawing Sheets

PROCESS FOR MANUFACTURING PROSTETIC DENTAL RECONSTRUCTIONS

BACKGROUND OF THE INVENTION

1. Field of the Invention

The invention is in the field of prosthetic dental reconstructions.

2. Description of the Background Art

Dental prostheses are understood here to refer to prosthetic dental inlays, prosthetic dental crowns and bridges, structural elements of all types, such as abutments (spacers), and dental devices of all types, with the invention relating especially to framework structures that may or may not be veneered.

A number of methods involving the production of prosthetic dental inlays or prosthetic dental crowns are known in the art. Generally following the grinding down of the dental defect, an impression is made of the tooth, the area around the tooth, and the jaw; the surface of the cavity may also be recorded on a computer using a stereophotogrammetric scanning device or laser scanning device. The desired external form of the inlay or crown is either reconstructed using a computer-assisted triaxial grinding machine, with the data on the tooth that were gathered and stored prior to the grinding down of the tooth defect, and is then cut directly from a suitable block of material, such as a ceramic block; or is fashioned out of plastic or plaster using models made from the impression that was taken of the untreated tooth.

The conventional technique of using a precious metal or a Ni—Cr alloy to produce an inlay or a crown involves certain aesthetic difficulties, which may be countered by overfiring the metal cap with a ceramic layer. This process, however, is awkward in terms of production mechanics and is susceptible to waste. Additionally, this method makes further monitoring of the condition of the tooth via x-rays impossible, which is considered a disadvantage, particularly in the case of crowns.

The growing demand for aesthetically restorative dental prostheses has advanced the use of other materials and methods, such as high-strength glass, which is poured in liquid form into a refractory mold and is then fired; or the firing of ceramic powder onto a refractory model. Such methods produce inlays and crowns that are aesthetically responsive and characterized by a high degree of x-ray opacity.

Ceramic prostheses that are cut out of ceramic blanks can, however, tend to break off as a result of handling—particularly in their marginal areas, which, in order to yield a seamless transition to the surviving tooth, must be as thin as possible. In addition, grinding traces—which are possible even with precision finishing—can lead to the formation of fissures, and thus to further risk of breakage.

In contrast, a method is specified in U.S. Pat. No. 5,106,303 in which ceramic powder compact is presintered. The form for the inlay or the crown is then profiled from this prepared block of material and is cut in enlarged dimensions to compensate for the shrinkage that will result from the subsequent sintering. Thus, the resulting dental prosthesis will fit into the prepared cavity or onto the prepared tooth stump. The advantage of this method is that the material can be processed in its so-called green state, which makes it easier to work with, since the density and hardness of the material necessary for its use as a dental prosthesis are achieved only after resintering.

Problems can result, however, from the method specified in U.S. Pat. No. 5,106,303 in that during the resintering process, which is performed at a temperature of ca. 1500° C., the very thin marginal areas may become deformed or susceptible to fractures.

SUMMARY OF THE INVENTION

Overcoming the problems associated with the methods presented above is the fundamental objective of the present invention.

Because the enlarged form produced from a pretreated reconstructive material is positioned for subsequent treatment on the working stump and/or within a working pack, which is also enlarged by one and the same enlargement ratio, wherein the material of the working stump or the working pack possesses a shrinkage factor that is basically equal to that of the reconstructive material, this form becomes completely stabilized during the subsequent treatment—in which shrinkage of the form that is dependent upon the material or the treatment takes place—and this protects against the above-mentioned damage resulting from handling, even in the critical marginal areas. And encasing the presintered form with a working pack of this type permits control of the shrinking process.

If an oxide ceramic, such as $ZrO_2$ or $Al_2O_3$, is used as the reconstructive material, and preferably also as the material for the working stump or the working pack, then the prosthetic dental reconstruction that is produced will exhibit a high degree of stability and density and a low level of porosity, with x-ray opacity and a choice coloration desirable for overall aesthetic impression.

According to the present invention, other hard materials are also suitable to be used as reconstructive materials or as materials for the working stump or the working pack, such as SiC, TiN, TiC, $TiB_2$, $Si_3N_4$, or other biocompatible carbides or nitrides from the $4^{th}$, $5^{th}$, or $6^{th}$ main groups, as well as mixtures or multicomponent systems of oxide ceramics, if necessary with different admixtures, such as is also specified in U.S. Pat. No. 5,106,303; but the process specified in the present invention is also suited to the use of pure feldspar ceramics, or so-called infiltration ceramics, that is, oxide ceramics, into which glass mass is infiltrated.

It is characteristic of oxide ceramics (and others of the above-mentioned hard materials) that molded parts produced as a result of a variety of hardening processes—compacting or presintering—possess a low level of density or stability and are easy to work with in this so-called green stage. If the form and, if necessary, the working stump or the working pack can be cut out of such a molded piece, this represents an advantage in terms of processing technique.

The method specified in the invention is also and especially advantageous for the production of abutments. Abutments that are sintered intermediately permit each form, which is equally complex, to be prepared during the integration phase of the fixture installation (implantation), and thereafter to be sintered, so that afterward—after the abutment has been set in—a direct incorporation of the crown or bridge is enabled. This is advantageous in terms of labor economics, as well as from the point of view of duration of treatment and aesthetic requirements, which are particularly applicable in the case of slender anchorage teeth.

If the material necessary for the working stump or the working pack is cut out of the molded part in a powder or chip form, and is pressed into the shape of the working stump or is packed around the presintered reconstruction form—especially as a prepared block mold—then this material is simply sintered together, more or less point by point, in the subsequent treatment, the resintering, in which the necessary compacting takes place, and can be eluted or released, or abraded out or off of the inlay or crown or from the finished, sintered reconstruction following sintering. To facilitate this, the form can be provided on its inner surface and/or on its outer surface with a thin layer of lacquer, for example a zapon or cellulose lacquer, as a parting compound, prior to placement on the working stump or packing into the working pack.

BRIEF DESCRIPTION OF THE DRAWINGS

Below, the invention is specified in detail, by example, with the help of diagrams, for the production of a crown form. The diagrams show.

DETAILED DESCRIPTION OF THE INVENTION

Figure 1A:
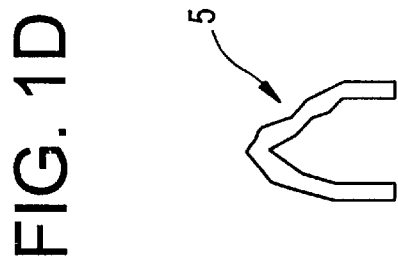
FIGS. 1a through 1e: the production of an enlarged crown form.
Figures 1B, 1C, 1D:
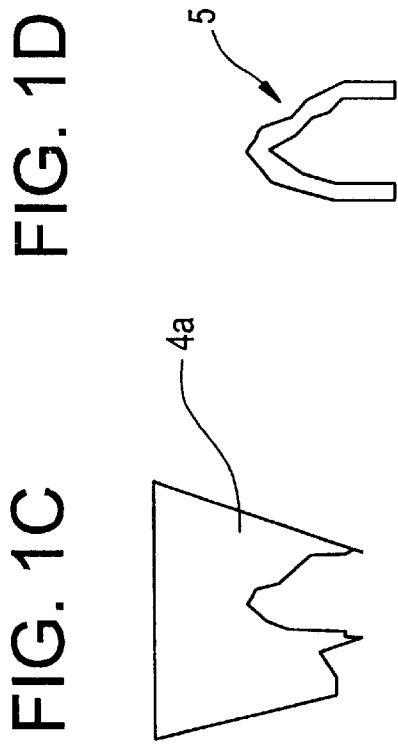
Figure 2:
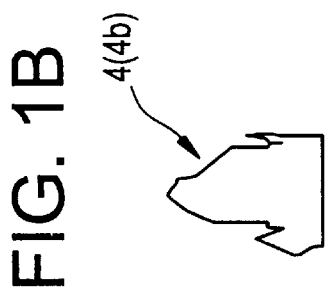
FIG. 2: a pretreated molded piece, from which the crown form and the material for a working stump or a working pack will be produced.

In FIGS. 1a through 1e, the production of an enlarged crown form 2—as an example for the production of inlays, dental units, bridges, and for reconstructions in general—can be seen. A carious tooth 3 is ground down to form a prepared tooth stump 4, from which an impression 4a is taken. The 8 impression 4a is then filled with a casting material. The resulting model 4b (which corresponds to the prepared tooth stump 4) of the cavity or the tooth condition then serves as the basis for the shaping of a wax or plastic model 5 for the crown. This wax model 5 is then scanned using a copy-milling system 6—for example via a laser distance device 7—(use of conventional, manual, or optical scanning via a pantograph system or some other suitable system is also possible), the data are stored in a computer 9, processed, and, enlarged appropriately for the material being used, transmitted to a milling spindle 8, which cuts a representation of the wax model 5 out of an oxide ceramic molded piece 10, enlarged by the appropriate enlargement factor. As was described above, the intermediate step of preparing a wax or plastic model may be omitted, and the form can be directly modeled using computer assisted means. After the cutting of the upper side of the crown form 2 (FIG. 2), the inside shape is produced in the same manner.

As was described in the introduction, the taking of an impression and the production of a model can also be omitted if the outer shape of the inlay, the shape of the cavity, or the shape of prepared teeth are recorded using appropriate scanning devices directly in the mouth of the patient.

In FIG. 2a molded piece 10 is illustrated, which has been compacted, for example, at room temperature, at approximately 2,000 bar. From the molded piece 10, for example zircon oxide ceramic, shavings 11, for example in a length of 2/10 mm, are milled off via cutting. In the manner described above in reference to FIGS. 1a–1e, the crown form 2 is produced.

In place of the shavings 11, powder material having particle sizes, for example, of, for example [sic], 30 to 500 $\mu$m may be used.

The crown form 2 and the shavings 11 are now presintered, for zircon oxide ceramics at approx. 1180° C. If necessary, the crown form 2 and the shavings 11 may also be produced from an already presintered molded piece 10.

Working with the ceramic material in its so-called green state, that is, in a non-presintered state, and working with the material in a half-sintered (presintered) state, have the advantage over methods that produce the desired prosthetic dental forms or reconstructions directly from the finally sintered working block via cutting that in processing the ceramic fewer micro cracks become incorporated in the surface, and the naturally high level of tool abrasion that occurs in the processing of the high-strength materials is reduced.

Figure 3:
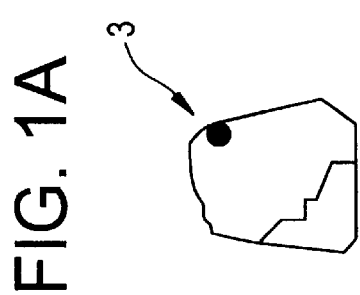
FIG. 3: a crown form resting on top of a working stump, and a dental crown obtained from further treatment.
Figure 1E:
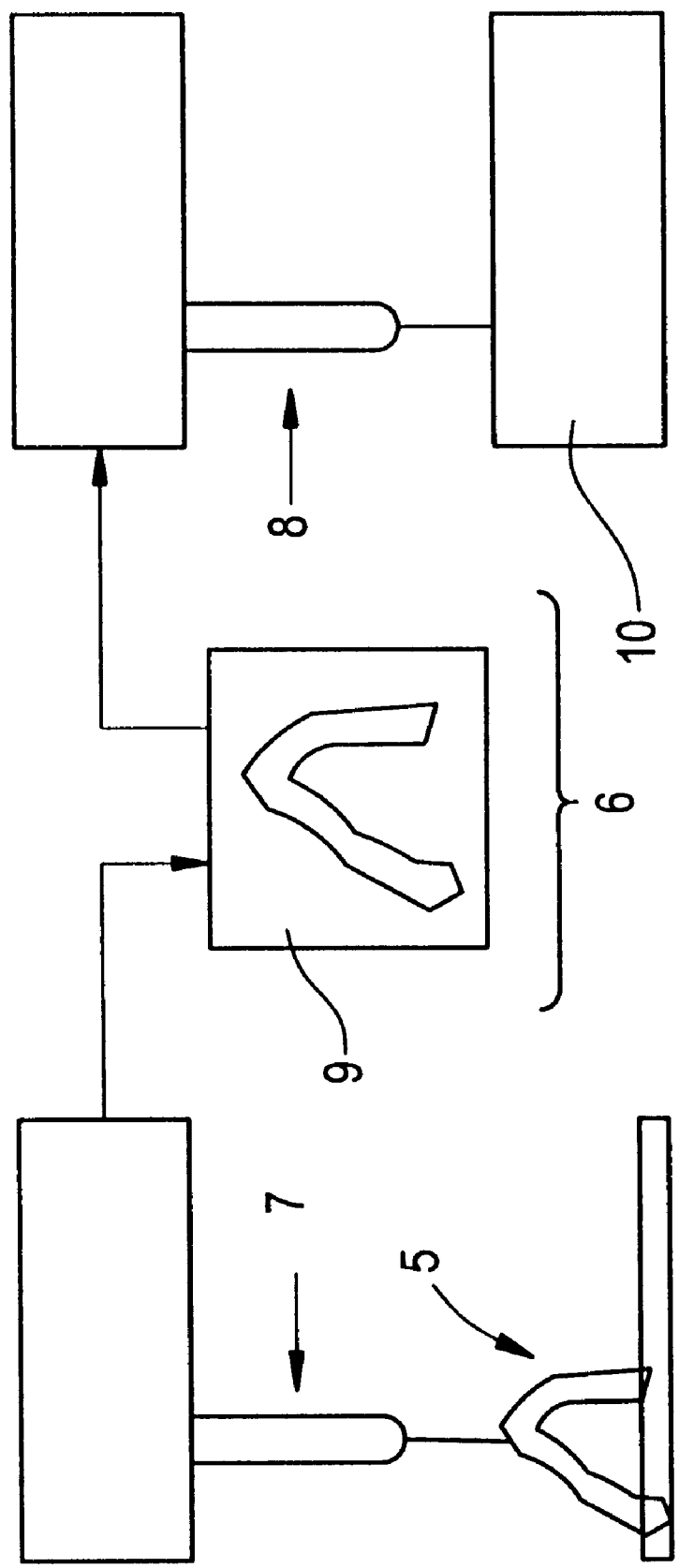

As illustrated in FIG. 3, the shavings 11 are then mixed with water to form a thick paste—such as can be used to form a working stump 12—which is filled into the crown form 2. The water that is added to the shavings 11 or the powder grains may contain various admixtures; for example, with an admixture of approx. 1% acetic acid, the handling of the paste is facilitated, resulting in a thixotropic performance. With the admixture of alcohols, for example, the stability or the compactness of the mixture can be increased. The type and quantity of the admixtures are to be selected based upon the desired or required properties. A thin layer of lacquer 13, 10 to 50 $\mu$, applied to the inner side of the crown form 2, closes the pores in the surface of the inner side and serves as a parting compound for the working stump 12. In the subsequent resintering, which is implemented for zircon oxide at a temperature of approx. 1500° C., and causes the same amount of shrinkage in the crown form 2 and the working stump 12, the lacquer 13 burns without residue, with a minimal gap forming between the crown form 2 and the working stump 12, so that the working stump can be easily removed from the crown form 2, or—particularly due to its porous consistency—can be blasted off.

As is indicated in FIG. 3 with a dotted line, the crown form 2—for the controlled support of the sintering-shrinkage process—may also lie within a working pack 14 of predetermined dimensions. The crown form 2 is then coated on the outside with the parting layer of lacquer, as described above. The working pack, which may be in block form, is then finally sintered together with the crown form and the working stump that may be positioned inside it. The sintering process can be well controlled with such a working pack, since the changes in the outside dimensions permit direct control of the shrinkage process. It goes without saying that other reconstructive forms which may have no, or only the smallest, hollow cavities, such as abutments, can be finally sintered, if necessary, only packed in the working pack.

The final dental crown (not shown) obtained in this manner, or the framework structure for the crown, fits precisely onto the prepared tooth stump 4 (FIG. 1). If desired, it may be veneered via known-in-the-art methods, at approx. 700 to 1200° C., using feldspar ceramic, glass ceramics, or zircon-containing veneer materials in powder form. If this is the case, the veneer material must be selected to correspond to the coefficient of thermal expansion of the crown or framework materials; the coefficient of thermal expansion of the veneer materials should lie within the corresponding range, or slightly below this range.

Effective in terms of time and aesthetically particularly responsive results are obtained when the known-in-the-art hot-press method is used, in which the veneer ceramic is applied in a hot, plastic, formable state. To this end, the outer form of the framework structure, to which a layer of color may already have been preliminarily applied to correspond to the desired tooth color, is constructed in wax; the framework structure is then embedded in a refractory pack that is heated to 800° C. Following application of the veneer materials, the temperature is increased to a level that is 100 to 300° C. below the sintering temperature for the framework structure, in order to prevent deformations of the latter. The now plastic veneer mass is pressed onto the framework structure. The veneer material blanks are advantageously already colored with enamel colors, whitish-translucent, to match the color of the enamel of natural teeth. In order that the framework structure can be veneered with wax prior to the pressing on of the veneer materials, functional conditions of the finished tooth may be incorporated.

Below, various enlargement factors, based upon the type of pretreatment used, for the production of a crown form 2 (FIG. 2), are given for zircon and aluminum oxide, as an example:

|  | Enlargement factor (ca) for | |
| --- | --- | --- |
| Pretreatment: | zircon oxide | aluminum oxide |
| not presintered, isostatically pressed | 30% | 20% |
| presintered at 1080° C. | 27% | 16% |
| 1100° C. | 26% | 15% |
| 1150° C. | 21% | 11% |
| 1200° C. | 13% | 7% |

As can be seen from the above table, which gives data on zircon and aluminum oxide as an example for possible other materials or alloys, a crown form produced from zircon oxide in accordance with FIG. 1 can also be further treated on a working stump made of aluminum oxide shavings, as long as the shrinkage that will occur as a result of the subsequent treatment is the same for both. The fact that this is dependent upon the type of pretreatment used is apparent from the above table.

It is also apparent that—as mentioned in the introduction—other materials may also be used in the production of the crown form, as well as in the production of the working stump or the working pack. For example, an alloy of 95% $ZrO_2$ and 5% yttrium oxide may be used.

The working stump or the working pack may also be designed as a single piece, as long as it can be flawlessly removed from the crown form following the subsequent processing—if necessary by means of a separating agent applied in the meantime—or blasted off following heat treatment.

What is claimed is:

1. A method for producing a dental prosthesis to be fitted to a fitting member, the fitting member comprising a corresponding anatomical dental feature within a patient's mouth, an abutment, or a corresponding mounting, said method comprising:

determining the three-dimensional contours of the fitting member, producing a three-dimensional form of the dental prosthesis, enlarged by a predetermined enlargement factor, from a presintered and/or compacted tooth replacement material, producing 1) a working stump that is enlarged by said predetermined enlargement factor and which corresponds to a portion of the three-dimensional contours of the fitting member; and/or 2) a working pack that is enlarged by the predetermined enlargement factor and which corresponds to a portion of the three-dimensional contour of the outer shape of the form; said working stump and/or said working pack being produced from a material which has approximately the same shrinkage factor as the tooth replacement material, placing the working stump in the form and/or packing the working pack around the outside of the form to completely cover the form, sintering the form with the working stump and/or the working pack, whereby the form is stabilized and becomes said dental prosthesis during said sintering, and separating the working stump and/or the working pack from the dental prosthesis after said sintering.

2. The method of claim 1, wherein the tooth replacement material and the material used to produce the working stump and/or to produce the working pack is a hard material selected from the group consisting of oxide ceramic, nitride, carbide, and an alloy of an oxide ceramic.

3. The method of claim 2, wherein the hard material is compacted into a green state and/or presintered at a temperature of between 1000 and 1300° C.

4. The method of claim 2, wherein the material used to produce the working stump and/or to produce the working pack is comprised of compacted and/or presintered oxide ceramic.

5. The method of claim 4, wherein the compacted and/or presintered material used to produce the working stump and/or to produce the working pack is in the form of a powder or shavings.

6. The method of claim 1, further comprising coating the form with a thin layer of a parting compound prior to associating the working stump and/or the working pack therewith.

7. The method of claim 2, wherein the form and the working stump and/or the working pack are sintered at a sintering temperature that is appropriate for the tooth replacement material.

8. The method of claim 1, further comprising providing the form with a veneer after separation of the working stump and/or the working pack therefrom.

* * * * *